United States Patent [19]

McCully

[11] Patent Number: 5,565,558
[45] Date of Patent: Oct. 15, 1996

[54] THIORETINACO OZONIDE AND ENHANCED BIOLOGICAL ACTIVITY OF THIORETINACO OZONIDE IN COMBINATION WITH INTERFERON

[76] Inventor: Kilmer S. McCully, 15 Wildwood St., Winchester, Mass. 01890

[21] Appl. No.: 366,638

[22] Filed: Dec. 30, 1994

[51] Int. Cl.$^6$ .................. C07H 19/167; A61K 31/365; C07D 411/00; C07D 333/20
[52] U.S. Cl. .................. 536/26.4; 536/26.41; 549/3; 549/29; 549/60; 556/138
[58] Field of Search .................. 530/351; 424/85.4, 424/85.5, 85.6, 85.7; 536/26.4, 26.41; 549/3, 29, 60; 556/138

[56] References Cited

U.S. PATENT DOCUMENTS

| | | | |
|---|---|---|---|
| 4,255,443 | 3/1981 | McCully | 424/275 |
| 4,383,994 | 5/1983 | McCully | 424/245 |
| 4,618,685 | 10/1986 | McCully | 549/63 |
| 4,925,931 | 5/1990 | McCully | 536/25 |

OTHER PUBLICATIONS

Kilmer S. McCully, "Homocysteine Thiolactone Metabolism in Malignant Cells," Cancer Research 36:3198–3202, 1976.

McCully et al., "Homocysteine Thiolactone in Arteriosclerosis and Cancer," Research Communications in Chemical Pathology and Pharmacology 59:107–119, 1988.

Jakubowski et al., "Synthesis of Homocysteine Thiolactone by Methionyl–t–RNA Synthetase in Cultured Mammalian Cells," FEBS Letters 317:237–240, 1993.

Kilmer S. McCully, "Chemical Pathology of Homocysteine. I Atherogenesis," Annals of Clinical and Laboratory Science 23:477–493, 1993.

McCully et al., "Chemopreventive and antineoplastic Activity of N–homocysteine Thiolactonyl Retinamide," Carcinogenesis 8:1559–1562, 1987.

McCully et al., "Chemopreventive Effect of N–Homocysteine Thiolactonyl Retinamido Cobalamin on Carcinogenesis By Ethyl Carbamate In Mice," Proceedings of the society for Experimental Biology and Medicine 191:346–351, 1989.

Olszewski et al., "Homocysteine Metabolism and the Oxidative Modification of Proteins and Lipids," Free Radical Biology and Medicine 14:683–693, 1993.

McCully et al., "Effect of the Synthetic N–homocysteine Thiolactonyl Derivatives, Thioretinaco, Thioretinamide, and Thioco on Growth and Lactate Production by Malignant Cells," Research Communications in Chemical Pathology and Pharmacology 77:125–128, 1992.

McCully et al., "Homocysteine and Lipid Metabolism in Atherogenesis: Effect of the Homocysteine Thiolactonyl Derivatives, Thioretinaco and Thioretinamide," Atherosclerosis 83:197–206, 1990.

McCully et al., "Inhibition of Neoplastic Growth by N–homocysteine Thiolactonyl Retinaamido Cobalamin," Research Communications in Chemical Pathology and Pharmacology 66:117–122, 1989.

Robert M. Friedman, *Interferons. A Primer.* Academic Press, New York, 1981.

Bonvini et al., "Selective Augmentation by Recombinant Interferon Gamma of the Intracellular Content of S–adenosylmethionine in Murine Macrophages," Journal of Immunology 136:2596–2604, 1986.

Brouty–Boye et al., "Retinoic Acid or Methionine Enhance Interferon's Inhibition of the Transformed Phenotype With No Effect on Tumorigenicity," Journal of Biological Regulators and Homeostatic Agents 2:45–49, 1988.

Bocci et al., "Studies on the Biological Effects of Ozone. I Induction of Interferon Gamma On Human Leucocytes," Haematologica 75:510–515, 1990.

Dziedzic et al., "Quantitation of Ozone–Induced Lung Lesion Density After Treatment With an Interferon Inducer Or An Anti–Inteferon Antibody," Toxicology Letters 39:51–62, 1987.

Higueras et al., "Interferon Decreases Serum Lipid Peroxidation Products of Hepatitis C Patients," Free Radical Biology and Medicine 16:131–133, 1994.

Sweet et al., "Ozone Selectively Inhibits Growth of Human Cancel Cells," Science 209:931–933, 1980.

Last et al., "Modification by Ozone of Lung Tumor Development in Mice," Journal of the National Cancer Institute 78:149–154, 1987.

Pendino et al., "Enhanced Production of Nitric Oxide By Rat Alveolar Macrophages After Inhalation of a Pulmonary Irritant is Associated With Increased Expression of Nitric Oxide Synthase," Journal of Immunology 151:7196–7205, 1993.

Keller et al., "L–arginine–Dependent Reactive Nitrogen Intermediates As Mediators of Tumor Cell Killing By Activated Macrophages," Cancer Research 50:1421–1425, 1990.

McCully et al., "Homocysteine Theory of Arteriosclerosis," Atherosclerosis 22:215–227, 1975.

Everitt et al., "The Effects of Hypophysectomy and Continuous Food Restriction, Begun at Ages 70 and 400 Days On Collagen Aging, Proteinuria, Incidence of Pathology and Longevity in the Male Rat, " Mechanisms of Ageing And Development 12;161–172, 1980.

*Primary Examiner*—Ponnathapura Achutamurthy
*Attorney, Agent, or Firm*—Peter J. Georges

[57] ABSTRACT

Thioretinaco ozonide and enhancement of the anticarcinogenic, antineoplastic, antiviral, and antiaging activities of thioretinaco ozonide by use of membranergic compositions, specifically the polypeptide cytokines, alpha-interferon, beta-interferon, and gamma-interferon are described.

3 Claims, No Drawings

THIORETINACO OZONIDE AND ENHANCED BIOLOGICAL ACTIVITY OF THIORETINACO OZONIDE IN COMBINATION WITH INTERFERON

TECHNICAL FIELD

This invention relates to thioretinaco ozonide and to enhancement of the anticarcinogenic, antineoplastic, antiviral, and antiaging activities of thioretinaco ozonide by use of the polypeptide cytokines, alpha-interferon, beta-interferon, and gamma-interferon.

BACKGROUND

It is known in the art that homocysteine thiolactone, a metabolite of the essential amino acid, methionine, is metabolized abnormally in malignant cells, as reported in Cancer Research 36:3198–3202, 1976. Because malignant cells are unable to convert homocysteine thiolactone to sulfate ester, excess homocysteine thiolactone accumulates within the cells and reacts with the free amino groups of proteins, nucleic acids, glycosaminoglycans and other molecules, a reaction known as thiolation. Extracts of human malignant tumors contain free homocysteine thiolactone, but normal human tissues contain only trace amounts of the compound, as reported in Research Communications in Chemical Pathology and Pharmacology 59:107–119, 1988. The accumulation of homocysteine thiolactone within cultured malignant cells was shown to be catalyzed by an error-editing reaction that is dependent upon methionyl t-RNA synthase, as reported in FEBS Letters 317:237–240, 1993.

Malignant cells are also known to possess other characteristic abnormalities of methionine metabolism, as reviewed in Annals of Clinical and Laboratory Science 24:27–59, 1994. These abnormalities are (1) poor growth of cultured malignant cells in methionine-free media containing homocysteine and a methyl donor, (2) decreased synthesis of adenosyl methionine and increased synthesis of adenosyl homocysteine in malignant cells, (3) increased transmethylase activity in tumor tissue, (4) hypomethylation of DNA from tumor tissue, (5) prevention by methionine of carcinogenesis in mammals by ethionine or by a choline-deficient diet, and (6) inhibition of aerobic glycolysis of cultured malignant cells by growth in media with a high methionine concentration.

The cause of abnormal homocysteine thiolactone metabolism in malignant cells was suggested to be a deficiency of or failure to form an N-substituted derivative of homocysteine thiolactone, as discussed in Cancer Research 36:3198–3202, 1976. According to this concept, the function of this N-substituted homocysteine thiolactone derivative in normal cells is to prevent accumulation of homocysteine thiolactone, thereby preventing thiolation of free amino groups of proteins, nucleic acids, and glycosaminoglycans, and also thereby preventing the malignant growth state that is characteristic of cancer cells.

The identity of the N-substituted antineoplastic derivative of homocysteine thiolactone that prevents homocysteine thiolactone formation in malignant cells was elucidated by synthesis of the antineoplastic derivatives of homocysteine thiolactone, N-maleyl homocysteine thiolactone amide, N-maleamide homocysteine thiolactone amide, and rhodium trichloride oxalyl homocysteine thiolactone amide, as taught in U.S. Pat. No. 4,383,994. These results show that the antineoplastic homocysteine thiolactone derivative is (1) active in a lipid-soluble form, (2) contains a conjugated double bond system with a carbonyl group adjacent to the nitrogen atom of homocysteine thiolactone, and (3) forms a complex with a transition metal atom that enhances antineoplastic activity. As taught in U.S. Pat. Nos. 4,618,685 and 4,925,931, incorporated herein by reference thereto, homocysteine thiolactone reacts with retinoic acid to form N-homocysteine thiolactonyl retinamide (NHTR), known as thioretinamide, and thioretinamide reacts with cobalamin to form N-homocysteine thiolactonyl retinamido cobalamin $(NHTR)_2Cbl$, known as thioretinaco. Both thioretinamide and thioretinaco have anticarcinogenic and antineoplastic activities, as reported in Carcinogenesis 8:1559–1562, 1987 and Proceedings of the Society for Experimental Biology and Medicine 191:346–351, 1989.

In experiments with cultured malignant and normal cells, thioretinaco was found to have antiproliferative activity, and thioco, the complex of homocysteine thiolactone and cobalamin, was found to increase growth of both malignant and normal cells, as reported in Research Communications in Chemical Pathology and Pharmacology 77:125–128, 1992. Treatment of rabbits with thioretinamide or thioretinaco, while consuming an atherogenic diet, significantly increased the serum concentration of homocysteine and enhanced atherogenesis, as reported in Atherosclerosis 83:197–206, 1990. Intra-tumor administration of thioretinaco decreased the growth of human pancreatic adenocarcinomas in athymic mice, as reported in Research Communications in Chemical Pathology and Pharmacology 66:117–122, 1989.

Interferons alpha, beta and gamma are cytokines that are know to have antineoplastic, antiviral, and antiproliferative activities, as discussed in Interferons. A Primer. by R. M. Friedman, Academic Press, New York, 1981. Recombinant interferon gamma increases the intracellular content of adenosyl methionine in cultured macrophages, as reported in Journal of Immunology 136:2596–2604, 1986. In that study, the enhanced tumoricidal activity of macrophages activated by interferon gamma was attributed to increased intracellular adenosyl methionine. Methionine and retinoic acid enhance the antiproliferative effects of interferons alpha and beta in transformed and malignant cultured cells, as reported in Journal of Biological Regulators and Homeostatic Agents 2:45–49, 1988.

Treatment of blood with ozone increases the production of interferon gamma by leukocytes, as reported in Haematologica 75:510–515, 1990. Induction of interferon by poly I:C in mice exposed to ozone reduces the extent of lung damage, and anti-interferon antibody increases lung damage, showing an antioxidant activity of interferon, as reported in Toxicology Letters 39:51–62, 1987. Interferon therapy of human patients with hepatitis C infection decreases the concentration of serum lipid peroxidation products by an antioxidant effect, as reported in Free Radical Biology and Medicine 16:131–133, 1994.

Ozone selectively inhibits the growth of human cancer cells in culture, compared to its effect on normal human lung diploid fibroblasts, as reported in Science 209:931–933, 1980. Ozone decreases the carcinogenicity of urethan in producing pulmonary tumors in mice in a dose dependent manner, as reported in Journal of the National Cancer Institute 78:149–154, 1987. Treatment of rats with ozone increases the production of nitric oxide by inducible nitric oxide synthetase of pulmonary macrophages, and more nitric oxide was produced in rats treated with interferon gamma, as reported in Journal of Immunology 151:7196–7205, 1993. Synthesis of nitric oxide from arginine is believed to be responsible for the tumoricidal effect of activated macrophages, as reported in Cancer Research 50:1421–1425, 1990.

One aspect of the present invention relates to enhancing biological activity of thioretinaco by reaction with ozone and oxygen to form a thioretinaco ozonide disulfonium complex.

Because of its lipophilic thioretinamide groups, thioretinaco is bound to the lipid bilayer of normal cells, contains tetraene conjugated double bond systems and a carbonyl group adjacent to the nitrogen atom of homocysteine thiolactone, and forms an octahedral complex with the cobalt atom of cobalamin, as reviewed in Annals of Clinical and Laboratory Science 24:27–59, 1994.

In accordance with the present invention, thioretinaco is believed to participate in oxidative phosphorylation in normal cells by formation of thioretinaco ozonide disulfonium complexes with ozone, oxygen and adenosine triphosphate within mitochondrial membranes. According to this concept, electrons from electron transport particles and protons from $F_1F_0$ complexes, in the presence of dehydroascorbate, successively reduce the oxygen molecule that is bound to thioretinaco ozonide, catalyzing the stereospecific binding and release of adenosine triphosphate from the ATP synthetase of $F_1$ complexes. The normal function of thioretinaco ozonide in oxygen metabolism is to limit the oxidative damage by reactive oxygen radicals to cellular macromolecules. The loss of thioretinaco ozonide from the membranes of neoplastic and senescent cells is believed to explain the increased oxidative damage that is found in the macromolecular constituents of these cells.

Another important function of thioretinaco ozonide in normal cells is believed to be the stereospecific synthesis of adenosyl methionine from methionine and adenosine triphosphate that is bound to the ATP synthetase of $F_1$ complexes of mitochondrial membranes, as reviewed in Annals of Clinical and Laboratory Science 24:134–152, 1994. During cell division and growth of normal tissues, thioretinaco is believed to be reversibly converted to thioco, increasing intracellular free radical oxidants, and oxidizing glutathione and ascorbate. In this process, reactive oxygen species, such as superoxide, oxidize the sulfur atom of homocysteine thiolactone to sulfate, the precursor of the coenzyme, phosphoadenosine phosphosulfate, that sulfates the glycosaminoglycans of connective tissues during tissue growth.

The efficiency of homocysteine thiolactone metabolism declines with aging, explaining increased synthesis of homocysteine thiolactone, increased serum homocysteine concentration, and decreased serum adenosyl methionine during aging. These observations suggest and it is believed that thioretinaco ozonide is gradually lost from cellular membranes during the aging process. It is further believed, according to this concept, that the increasing risk of atherogenesis and carcinogenesis with aging is related to increased susceptibility to loss of thioretinaco ozonide by atherogenic factors and by carcinogenic factors.

Another aspect of the present invention also relates to further enhancement of biological activity of thioretinaco ozonide/thioretinaco ozonide disulfonium complex with the cytokines, alpha-, beta-, and gamma-interferons. The substantially enhanced anticarcinogenic, antineoplastic, antiviral, antiatherogenic, and antiaging activities of thioretinaco are believed to occur by specific stabilization and binding of thioretinaco ozonide by interferon within the membranes of treated cells. It is believed, according to this concept of my invention, that the concentration and activity of thioretinaco ozonide, combined with interferon, are increased within cell membranes. Because of this effect, the synthesis of adenosyl methionine from methionine is increased, and the synthesis of homocysteine thiolactone from methionine is decreased. Thus, treatment in accordance with the present invention, reverses the biochemical abnormalities in neoplasia, atherosclerosis, viral infections, autoimmune diseases, and aging, accounting for the enhanced biological activities of thioretinaco ozonide interferon complexes. In accordance with the present invention, the accumulation of reactive oxygen radicals is diminished, the thiolation of proteins, nucleic acids, and glycosaminoglycans by homocysteine thiolactone is diminished, thioco is converted to thioretinaco, diminishing the growth rate of affected cells, oxidative phosphorylation is increased, reversing the biochemical abnormalities of neoplastic cells, myointimal cells of atheromas, virally infected cells, and senescent cells. These multiple biochemical effects are believed to explain the enhanced anticarcinogenic, antineoplastic, antiviral and antiaging effects of thioretinaco ozonide by interferons, as taught in the present invention.

DESCRIPTION OF THE INVENTION

In one aspect, this invention relates to the novel compound thioretinaco ozonide. This compound may be formed by direct exposure of a solution of thioretinaco to an atmosphere enriched with ozone. Alternatively, thioretinaco may be administered to mammals, which are exposed to non-toxic concentrations of ozone in air, resulting in formation of thioretinaco ozonide within the tissues of a mammal.

In another aspect, this invention relates to formation of a complex, membrane-bound thioretinaco ozonide, within the tissues of a mammal. Formation of this complex occurs in two steps. First, thioretinaco reacts with ozone and oxygen to form thioretinaco ozonide oxygen disulfonium complex:

$$(NHTR)_2CbI+O_3 \rightarrow (NHTR)_2CbIO_3^{++}+2e^-$$

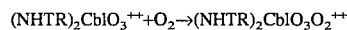

$$(NHTR)_2CbIO_3^{++}+O_2 \rightarrow (NHTR)_2CbIO_3O_2^{++}$$

where $(NHTR)_2CbI$ is thioretinaco $(NHTR)_2CbIO_3^{++}$ is thioretinaco ozonide, and $(NHTR)_2CbIO_3O_2^{++}$ is thioretinaco ozonide oxygen disulfonium complex.

Second, thioretinaco ozonide oxygen disulfonium complex becomes bound to cellular membranes, and interferons alpha, beta, or gamma stabilize and orient the complex within the membrane, enhancing its biochemical functions:

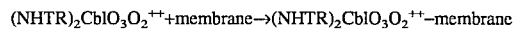

$$(NHTR)_2CbIO_3O_2^{++}+membrane \rightarrow (NHTR)_2CbIO_3O_2^{++}-membrane$$

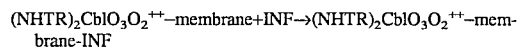

$$(NHTR)_2CbIO_3O_2^{++}-membrane+INF \rightarrow (NHTR)_2CbIO_3O_2^{++}-membrane-INF$$

where –membrane is the cellular membranes of affected cells, and INF is interferon alpha, beta, or gamma.

Operation of the subject complex of this invention, membrane bound thioretinaco ozonide oxygen disulfonium interferon, $(NHTR)_2CbIO_3O_2^{++}$–membrane-INF, occurs by (1) administration of thioretinaco to mammals that are exposed to non-toxic, moderate concentrations of ozone in air, followed by administration of interferons alpha, beta or gamma to the mammals, or (2) exposure of thioretinaco, dissolved in a suitable solvent, to ozone and oxygen, administration of the resulting thioretinaco ozonide oxygen disulfonium complex to mammals, followed by administration of interferons alpha, beta or gamma to the mammals.

In mammals exposed to carcinogenic chemicals, radiation, or oncogenic viruses, the subject complex of this invention, $(NHTR)_2O_3O_2$–membrane-INF, ameliorates/prevents the induction of benign or malignant neoplasms, In mammals with transplanted or spontaneous primary or metastatic malignant neoplasms, the complex of this invention inhibits growth and causes regression of these neoplasms. In mammals consuming an atherogenic diet, the complex of this invention prevents, delays, or causes regression of arteriosclerotic plaques of aorta and peripheral arteries. In mammals that are infected with pathogenic viruses, the complex of this invention inhibits replication of these viruses, prevents or causes regression of the pathogenic effects of these viruses, and prevents post-infection autoimmune sequelae of these viruses. In senescent mammals with degenerative aging changes of their tissues, decreased oxidative metabolism, and decreased life expectancy, the complex of this invention prolongs life span, prevents further degenerative changes of tissues, associated with aging, and enhances oxidative metabolism.

Thioretinaco can be prepared, as taught in U.S. Pat. No. 4,925,931, incorporated herein by reference thereto, by reaction of N-homocysteine thiolactonyl retinamide, known as thioretinamide, with 5' deoxyadenosyl cobalamin. Thioretinamide can be prepared, as taught in U.S. Pat. 4,618,685, incorporated herein by reference thereto, by reaction of the free base of homocysteine thiolactone with trans retinoic acid.

Thioretinaco ozonide, in combination with administration of interferons alpha, beta, or gamma, is effective in preventing chemical carcinogenesis in mammals, inhibiting growth of malignant tumors in mammals, decreasing atherogenesis in mammals, decreasing viral replication in cultured cells, decreasing the degenerative effects of aging in mammals, and extending the life span of mammals. Despite their efficacy in the aforesaid therapeutic effects, the method of use of the compositions of the present invention is non-toxic. In this respect, the compounds and processes of this invention do not suffer the drawback of many known antineoplastic, antiviral, antiatherogenic, and antiaging agents, which have cumulative toxic effects after prolonged administration. In particular, the use of interferons alpha, beta, or gamma, without simultaneous administration of thioretinaco ozonide, is limited by cumulative toxicity in prolonged courses of therapy.

According to this invention, thioretinaco ozonide, with simultaneous administration of interferon, prevents the formation of malignant cells in mammals by preventing the depletion of membrane bound thioretinaco ozonide by carcinogenic chemicals, radiation, or viruses. This invention restores the deficient synthesis of adenosyl methionine within malignant cells, virally infected cells, damaged myointimal cells of arteries, or senescent cells by restoring the deficient concentration and deficient formation of thioretinaco ozonide within cellular membranes.

The formation of thioretinaco ozonide by reaction of thioretinaco with ozone enhances by an order of magnitude the anticarcinogenic, antineoplastic, antiatherogenic, and antiproliferative activities against chemical carcinogenesis, neoplastic growth, induction of atherosclerosis, and growth of cultured cancer cells, respectively, compared to the corresponding biological activities of either thioretinaco or ozone acting alone. In addition, treatment of mammals or cell cultures with interferons alpha, beta, or gamma, simultaneously with thioretinaco ozonide further enhances these corresponding biological activities by an order of magnitude, compared to the effects of either thioretinaco ozonide or interferons alpha, beta, or gamma acting alone. The operation of the invention described herein, therefore, greatly increases the effectiveness of thioretinaco when used in combination with ozone and interferons alpha, beta, or gamma because of the greatly enhanced biological activity of thioretinaco ozonide oxygen disulfonium complex without undesirable toxic effects to the organs and tissues of the mammal undergoing treatment.

The invention described herein is also useful in treatment and prevention of neoplastic, atherosclerotic, or viral diseases, or degenerative diseases associated with senescence and aging in which interferon is replaced by other membranergic substances that enhance or modify the biological activity of thioretinaco ozonide oxygen disulfonium complexes within cell membranes. Such other substances may be administered in the manner and dosage as described herein for interferon. A membranergic substance is defined as a biologically active substance that enhances or modifies the activity of a functional complex of a cellular membrane. Membranergic substances that are useful in enhancing of modifying the activity of the invention described herein in place of interferon include, but are not limited to, ubiquinone, dehydrepiandrosterone, melatonin; cytokines, such as interleukin-1, interleukin-2, and tumor necrosis factor; polypeptide growth factors, such as insulin-like growth factor, erythropoietin, colony stimulating factor, nerve growth factor, granulocyte-macrophage growth factor, platelet derived growth factor, epidermal growth factor, and hepatocyte growth factor; and polypeptide factors that control cell division, such as cycline and cyclin-dependent kinases.

The compositions of the present invention find utility in treatment of mammalian diseases and specifically, based on the believed mechanisms herein described, are useful in preventing the occurrence of spontaneous human neoplasms, including, but not limited to, cancer of lung, skin, colon, breast, prostate, pancreas, brain, lymph nodes, liver, kidney or other organs that arise because of exposure of carcinogenic chemicals, radiation, viruses, dietary factors, or genetic factors. It is further believed that this invention is useful for the treatment of human neoplasms, primary or metastatic, by intratumor and parenteral administration, causing regression of and preventing metastasis of malignant neoplasms. It is also believed that this invention is useful in treatment of human atherosclerosis, involving aorta, coronary, renal, peripheral, or other major arteries, causing regression and preventing progression of atherosclerotic plaques, thereby preventing or ameliorating coronary heart disease, stroke, renovascular disease, and peripheral vascular disease. It is also believed that this invention is useful in treatment of human pathogenic viral infections, including, but not limited to, hepatitis virus, immuno-deficiency virus, hemorrhagic fever viruses, encephalitis virus, influenza viruses, rhinoviruses and enteric viruses, by preventing viral replication and spread of the virus infection within the cells of the various tissues of the body. It is also believed that this invention is useful in treatment of human degenerative diseases associated with aging, including, but not limited to, osteoarthritis, osteoporosis, cataract, prostatic hypertrophy, diabetes mellitus, rheumatoid arthritis, thyroiditis, lupus erythematosus, pernicious anemia and other autoimmune disorders, causing remission or preventing progression of these diseases within the tissues of the body. It is expected that this invention will be useful in prolonging human life span by preventing degenerative diseases of aging, including atherosclerosis, cancer, autoimmune disorders, and age-associated loss of function of brain, heart, lungs, liver, kidneys, and other major organs.

Therapeutic use of this invention allows for decreasing the induction of chemically induced tumors in mammals, decreasing the growth of malignant tumors in mammals, decreasing the induction of arteriosclerotic plaques in mammals, decreasing viral replication in mammals, preventing the degenerative tissue changes associated with aging in mammals, and extending the life span of mammals. Specifically, practice of this invention is considered useful for prevention of spontaneous human neoplasms, including, but not limited to, cancer of lung, skin, breast, prostate, colon, pancreas, brain, lymph nodes, liver, kidney or other organs that arise because of exposure to carcinogenic chemicals, radiation, viruses, dietary factors, or genetic factors.

Practice of this invention is also considered useful for treatment of mammalian and in particular human neoplasms, primary or metastatic, by intratumor, parenteral, or enteric administration, for treatment of human atherosclerosis, involving aorta, coronary, carotid, renal, peripheral, or other major arteries, for treatment of human pathogenic viral infections, for treatment of human degenerative diseases associated with aging, including, but not limited to, osteoarthritis, osteoporosis, cataract, prostatic hypertrophy, diabetes mellitus, rheumatoid arthritis, thyroiditis, lupus erythematosus, and pernicious anemia, and for prolonging human life span.

The compound of this invention can be used in admixture with conventional excipients, i.e., pharmaceutically and physiologically acceptable organic or inorganic carriers suitable for enteral, parenteral, or topical applications which do not deleteriously interact with the active compounds. Suitable pharmaceutically and physiologically acceptable carriers include, but are not limited to, water, salt solutions, alcohols, glycols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxymethyl cellulose, polyvinyl pyrrolidine, etc. The pharmaceutical preparations can be sterilized and, if desired, mixed with auxiliary agents, including lubricants, preservatives, stabilizers, wetting agents, emulsifiers, salts for influencing osmotic pressure, buffers, coloring, flavoring and/or aromatic substances and the like which do not deleteriously interact with the active compound.

Solutions, preferably glycol, oil or alcohol solutions, as well as suspensions, emulsions, or implants, including suppositories, can be used for parenteral application. Unit dosages can conveniently be provided in ampoules. It is preferred to administer the active compound intraperitoneally in the form of a solution in propylene glycol.

As heretofore noted, the invention described herein is useful in treatment and prevention of neoplastic, atherosclerotic, and viral diseases in mammals, generally. Specifically, it is contemplated that the present invention is useful for such treatment in human subjects. The range of effective concentration of thioretinaco ozonide oxygen disulfonium complex is broad, extending form 0.1–60 mg/kg of body weight. The subject invention can be administered to mammals or human subjects in the aforesaid dosage range. Such administration can be in a variety of compatible, non-toxic solvents and vehicles, including, but not limited to, propylene glycol, dimethyl sulfoxide, and ethanol. The subject invention can be administered by the enteric route, employing capsules, tablets, and time release formulations, mixed with suitable inert carriers. The subject invention can also be administered parenterally in compatible solvents and vehicles, given intravenously, intramuscularly, intraperitoneally, subcutaneously, intracisternally, intrathecally, and within neoplasms in various internal organs by direct injection, with ultrasound, nuclear magnetic resonance, or X-ray computerized tomography guidance. The biological activity of the subject invention is enhanced by simultaneous administration of interferons alpha, beta, or gamma, given parenterally in a wide range of dosages, from $1-10^3$ units/kg or given enterally in similar doses in solutions and with suitable vehicles and carriers. Surprisingly, the cumulative toxicity of interferons alpha, beta, or gamma is decreased when administered to mammals, including human subjects, simultaneously with thioretinaco ozonide oxygen disulfonium complex.

It will be appreciated that the actual preferred amount of active compound used will vary according to the specific isomer being used, the particular compositions formulated, the mode of application and particular site and organism being treated. Optimal application rates for a given set of conditions can be ascertained by those skilled in the art, using conventional dosage determination tests in view of the above guidelines.

EXAMPLE 1

To demonstrate anticarcinogenic activity, thioretinaco is formed by dissolving thioretinamide in 100 ml of ethanol with mixing at 37° C. and by adding 20 mg of 5' deoxyadenosyl cobalamin, to form a clear salmon pink solution. To form thioretinaco ozonide oxygen disulfonium complex, $(NHTR)_2CblO_3O_2^{++}$, the solution of thioretinaco in ethanol is exposed to a stream of oxygen enriched with ozone from an ultraviolet light generator or other suitable ozone generator. To transfer the resulting $(NHTR)_2CblO_3O_2^{++}$ to a non-volatile, non-toxic vehicle, such as propylene glycol, the solution is evaporated under reduced pressure at 37° C. to remove ethanol. The resulting clear, dark red-brown solution of $(NHTR)_2CblO_3O_2^{++}$ is administered intraperitoneally to A/J female mice. The mice are also injected with ethyl carbamate and with recombinant interferon gamma for 16 weeks, according to the following protocol: The day prior to each of the first of 10 weekly injections, 2 mg of ethyl carbamate in 0.2 ml of water, is injected intraperitoneally, giving a total dose of 20 mg/mammal. The mammals are also injected intraperitoneally on different days with $(NHTR)_2CblO_3O_2^{++}$ and with recombinant interferon gamma weekly. The mammals are weighed weekly, and after 16 weeks the lungs are dissected, fixed in 10% formalin, and the number of pulmonary tumors is determined by examination in a dissecting microscope. This example illustrates projected percentage of tumors induced reflected by anticipated relative values as shown.

| Compound | Total Dose (mg/kg) | Dose of INF-gamma | Tumors Induced |
|---|---|---|---|
| vehicle only | — | — | 100% |
| $(NHTR)_2Cbl$ | 60 | — | 75% |
| $(NHTR)_2CblO_3O_2^{++}$ | 60 | — | 10% |
| $(NHTR)_2CblO_3O_2^{++}$ | 60 | $10^3$ units | 1% |

Formation of pulmonary neoplasms, induced by ethyl carbamate in A/J mice, is inhibited by use of thioretinaco, is further inhibited by use of thioretinaco ozonide oxygen disulfonium complex, and is inhibited to even greater extent by use of thioretinaco ozonide oxygen disulfonium-membrane-INF gamma.

EXAMPLE 2

Thioretinaco is prepared and administered to A/J mice given ethyl carbamate, as in Example 1. Groups of mammals are exposed to an atmosphere containing 0.8 ppm of ozone, $10^3$ units of interferon alpha, $10^3$ units of interferon beta, or $10^3$ units of interferon gamma, injected subcutaneously, as indicated in the table.

| Compound | Ozone, 0.8 ppm | INF, $10^3$ Units | Tumors Induced |
|---|---|---|---|
| vehicle only | − | — | 100% |
| vehicle only | + | — | 70% |
| $(NHTR)_2Cbl$ | − | — | 75% |
| $(NHTR)_2Cbl$ | + | — | 40% |
| $(NHTR)_2Cbl$ | + | INF alpha | 2% |
| $(NHTR)_2Cbl$ | + | INF beta | 3% |
| $(NHTR)_2Cbl$ | + | INF gamma | 1% |

The relative anticipated values or tumors induced according to this example shows that formation of pulmonary neoplasms, induced by ethyl carbamate in A/J mice, is inhibited in mammals given thioretinaco, while inspiring an atmosphere containing ozone, and given injections of interferons alpha, beta, or gamma.

EXAMPLE 3

Thioretinaco ozonide oxygen disulfonium complex is prepared, as described in example 1. Human pancreatic adenocarcinoma cells ($10^5$) are injected subcutaneously in athymic mice, producing palpable neoplasms after 10–14 days. Solutions of thioretinaco ozonide oxygen disulfonium complex in propylene glycol are injected directly into the growing neoplasms. Weekly injections of interferon gamma ($10^3$) are given intraperitoneally. Alternatively, the solutions of thioretinaco ozonide oxygen disulfonium complex are given intraperitoneally each week for 6 weeks, beginning the day after subcutaneous injection of adenocarcinoma cells. After 6 weeks, the mammals are sacrificed, and the tumors are dissected and weighed. As indicated in the table, tumor weights are reflected by the anticipated relative values shown.

| Compound | Total Dose (mg/kg) | Dose of INF-gamma | Tumors Weight (mg) |
|---|---|---|---|
| vehicle only | — | — | 1.00 |
| $(NHTR)_2Cbl$ | 2.5 (intratumor) | — | 0.50 |
| $(NHTR)_2CblO_3O_2^{++}$ | 2.5 (intratumor) | — | 0.05 |
| $(NHTR)_2CblO_3O_2^{++}$ | 2.5 (intratumor) | $10^3 \times 6$ | 0.01 |
| $(NHTR)_2Cbl$ | 15 (i.p.) | — | 0.60 |
| $(NHTR)_2CblO_3O_2^{++}$ | 15 (i.p.) | — | 0.10 |
| $(NHTR)_2CblO_3O_2^{++}$ | 15 (i.p.) | $10^3 \times 6$ | 0.01 |

The growth of human malignant neoplasms in athymic mice is inhibited by injection of thioretinaco, growth inhibition is enhanced by injection of retinaco ozonide oxygen disulfonium complex, and interferon gamma injections further enhance growth inhibition of thioretinaco ozonide oxygen disulfonium complex.

EXAMPLE 4

Thioretinaco ozonide oxygen disulfonium complex is prepared, as described in Example 1. Mouse L cells in culture are treated with interferon alpha, beta, or gamma for 4 hours, the interferon is removed by cell washing, and the cells are infected with EMC virus at a multiplicity of 10:1. After 14 hours, the culture fluids, containing thioretinaco ozonide oxygen disulfonium complex, are harvested and assayed for virus particles. As indicated in the table, virus titers are reflected by the anticipated relative values.

| Compound | Concentration (mg/dl media) | INF (units) | Virus Titer ($\log_{10}$) |
|---|---|---|---|
| vehicle only | — | — | 2.0 |
| vehicle only | — | alpha ($10^2$) | 1.0 |
| vehicle only | — | beta ($10^2$) | 1.2 |
| vehicle only | — | gamma ($10^2$) | 1.25 |
| $(NHTR)_2CblO_3O_2^{++}$ | 1.0 | — | 1.0 |
| $(NHTR)_2CblO_3O_2^{++}$ | 1.0 | alpha ($10^2$) | 0.05 |
| $(NHTR)_2CblO_3O_2^{++}$ | 1.0 | beta ($10^2$) | 0.10 |
| $(NHTR)_2CblO_3O_2^{++}$ | 1.0 | gamma ($10^2$) | 0.12 |

Viral replication within cultured cells is inhibited by exposure to thioretinaco ozonide oxygen disulfonium complex and such inhibition is augmented by interferons alpha, beta, and gamma.

EXAMPLE 5

Thioretinaco is prepared, as described in Example 1, and dissolved in a suitable solvent. Rabbits are fed a synthetic diet containing homocystine oxidized with hydrogen peroxide, as described in Atherosclerosis 22:215–227, 1975. Weekly injections of thioretinaco and interferon gamma are given intraperitoneally for 24 weeks. Rabbits are housed in cages with ambient air or with air enriched with ozone, 0.5 ppm. After 24 weeks, the mammals are sacrificed, and the percentage of aortic intimal surface involved with arteriosclerotic plaques is determined morphometrically, as described in Atherosclerosis 83:197–206, 1990. Relative values for anticipated plaque area percentages are shown.

| Thioretinaco (mg) | Ozone (0.5 ppm) | INF gamma ($10^3$ Units) | Plaque Area (%) |
|---|---|---|---|
| — | − | − | 25% |
| — | + | + | 20% |
| 12 | − | − | 20% |
| 12 | + | − | 5% |
| 12 | + | + | 1% |

Exposure of mammals consuming an atherogenic diet to atmospheric ozone increases the antiatherogenic effect of thioretinaco and injection of interferon gamma in addition to thioretinaco greatly enhances the antiatherogenic effect of thioretinaco.

EXAMPLE 6

Thioretinaco ozonide oxygen disulfonium complex is prepared, as described in Example 1 and dissolved in a suitable solvent. Male Wistar rats, aged 400 days, are fed ad libitum (ad lib) or food restricted (FR) for 800 days, as described in Mechanisms of Ageing and Development 12:161–172, 1980. Mammals are injected intraperitoneally every 20 days with thioretinaco ozonide oxygen disulfonium complex, followed by injections 6 hours later with interferon alpha. An approximate anticipated percentage of live mammals, determined at 800 days of age and 1200 days of age, is shown in the table.

| Diet | $(NHTR)_2CblO_3O_2^{++}$ (mg/kg) | INF alpha (units) | 800 days (%) | 1200 days (%) |
|---|---|---|---|---|
| ad lib | — | — | 40% | 0% |
| FR | — | — | 60% | 10% |
| ad lib | 40 | — | 75% | 15% |
| ad lib | 40 | $10^3 \times 40$ | 90% | 25% |

The life span of rats is prolonged more where thioretinaco ozonide oxygen disulfonium complex is administered to such rats than when their food is restricted. Simultaneous treatment with interferon alpha augments the antiaging activity of thioretinaco ozonide oxygen disulfonium complex.

EXAMPLE 7

The thioretinaco ozonides of the present invention, alone or in combination with interferons alpha, beta, and/or gamma, inhibit cell proliferation and this Example represents an application of such compounds of the invention to inhibit cell proliferation.

Thioretinaco ozonide oxygen disulfonium complex is prepared, as described in Example 1 and dissolved in a suitable solvent. Human pancreatic adenocarcinoma cells (RWP-2) are cultured in RPMI 1640 medium (Gibco) with 12.5% fetal bovine serum and with added penicillin, streptomycin, fungizone, amphotericin, and garamycin, as described in Research Communications in Chemical Pathology and Pharmacology 77:125–128, 1992. The number of cells per dish is determined after culture for 4 days in the presence of thioretinaco ozonide oxygen disulfonium complex with the simultaneous addition of interferons alpha, beta, or gamma to the culture medium.

| Compound | Concentration (mg/ml media) | INF (units) | Cell number $(10^{-5}/$ dish) |
|---|---|---|---|
| vehicle only | — | — | 7.5 |
| vehicle only | — | alpha ($10^2$) | 1.5 |
| vehicle only | — | beta ($10^2$) | 1.5 |
| vehicle only | — | gamma ($10^2$) | 1.0 |
| $(NHTR)_2CblO_3O_2^{++}$ | 1.0 | — | 2.5 |
| $(NHTR)_2CblO_3O_2^{++}$ | 1.0 | alpha ($10^2$) | 0.5 |
| $(NHTR)_2CblO_3O_2^{++}$ | 1.0 | beta ($10^2$) | 0.5 |
| $(NHTR)_2CblO_3O_2^{++}$ | 1.0 | gamma ($10^2$) | 0.2 |

The growth of human pancreatic adenocarcinoma cells in culture is inhibited, when thioretinaco ozonide oxygen disulfonium complex is added to the culture medium. Interferons alpha, beta, and gamma also inhibit growth of human pancreatic adenocarcinoma cells. When thioretinaco ozonide oxygen disulfonium complex and interferons alpha, beta, and gamma are simultaneously present in the cell culture medium there is a high level inhibitory effect on cell growth. The projected cell member values are illustrative of the expected order of inhibition the invention will provide.

The compounds herein described and the processes for their use in combination with interferons and ozone that establish antineoplastic, antiproliferative, and antiviral activities are expected to be effective in preventing chemically induced tumors in laboratory mice, diminishing growth of malignant tumors in laboratory mice, preventing arteriosclerosis in laboratory rabbits, diminishing the replication of a virus in cultured mouse cells, and increasing the life span of laboratory rats. The compounds and processes of this invention are also considered to have value as therapeutic agents and treatments in preventing human cancer, decreasing the growth of human malignant tumors, preventing human arteriosclerotic plaques, diminishing the replication of human pathogenic viruses, preventing the degenerative tissue abnormalities associated with human aging, and extending the human lifespan.

The invention described herein is useful in treatment and prevention of neoplastic, atherosclerotic, and viral diseases in mammals generally, specifically, human subjects. The range of effective concentration of thioretinaco ozonide oxygen disulfonium complex is broad, extending from 0.1–60 mg/kg of body weight. The subject invention can be administered to mammals or human subjects in the aforesaid dosage range. Such administration can be in a variety of compatible, non-toxic solvents and vehicles, including, but not limited to, propylene glycol, dimethyl sulfoxide, and ethanol. The subject invention can be administered by the enteric route, employing capsules, tablets, and time release formulations, mixed with suitable inert carriers. The subject invention can also be administered parenterally in compatible solvents and vehicles, given intravenously, intramuscularly, intraperitoneally, subcutaneously, intracisternally, intrathecally, and within neoplasms in various internal organs by direct injection, with ultrasound, nuclear magnetic resonance, or X-ray computerized tomography guidance. The biological activity of the subject invention is enhanced by simultaneous administration of interferons alpha, beta, or gamma, given parenterally in a wide range of dosages, from $1–10^3$ units/kg or given enterally in similar doses in solutions and with suitable vehicles and carriers. Surprisingly, the cumulative toxicity of interferons alpha, beta, or gamma is decreased when administered to mammals, including human subjects, simultaneously with thioretinaco ozonide oxygen disulfonium complex.

It is expected that the invention, as illustrated in the preceding synthetic examples, can be repeated with comparable levels of success by substituting the generically or specifically described compounds and processes of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

I claim:

1. N-Homocysteine thiolactonyl retinamido cobalamin ozonide, having the formula $(NHTR)_2CblO_3$, wherein NHTR is N-homocysteine thiolactonyl retinamide, Cbl is cobalamin, and $O_3$ is ozone.

2. A process for preparing the compound of claim 1, comprising allowing one mole of N-Homocysteine thiolactonyl retinamido cobalamin to react with about one mole of ozone.

3. N-Homocysteine thiolactonyl retinamido cobalamin ozonide oxygen disulfonium complex.

* * * * *